United States Patent [19]
Wnuk et al.

[11] Patent Number: 5,520,875
[45] Date of Patent: May 28, 1996

[54] PROCESS FOR PRODUCING A SURFACTANT TREATED, FORMED, POLYMERIC WEB

[75] Inventors: Andrew J. Wnuk, Wyoming; Thurman J. Koger, II, Hamilton, both of Ohio

[73] Assignee: The Procter & Gamble Company, Cincinnati, Ohio

[21] Appl. No.: 498,727

[22] Filed: Aug. 2, 1995

Related U.S. Application Data

[63] Continuation of Ser. No. 204,112, Mar. 1, 1994, abandoned.

[51] Int. Cl.$^6$ ............................ B29C 47/06; B29D 9/00
[52] U.S. Cl. .................... 264/504; 264/557; 264/570; 264/571; 264/156; 264/173.15; 264/173.16; 264/173.18; 264/210.2; 264/280; 264/210.6
[58] Field of Search ...................... 264/504, 570, 264/571, 154, 156, 300, 557, 280, 284, 293, 173.15, 173.16, 173.18, 173.11, 173.12, 210.2, 210.6

[56] References Cited

U.S. PATENT DOCUMENTS

| | | | |
|---|---|---|---|
| 3,054,148 | 9/1962 | Zimmerli | 264/154 |
| 3,718,059 | 2/1973 | Clayton | 264/154 |
| 4,070,218 | 1/1978 | Weber | 264/300 |
| 4,151,240 | 4/1979 | Lucas et al. | 264/154 |
| 4,293,608 | 10/1981 | Isaka et al. | 428/220 |
| 4,317,792 | 3/1982 | Raley et al. | 264/504 |
| 4,342,314 | 8/1982 | Radel et al. | 128/287 |
| 4,456,570 | 6/1984 | Thomas et al. | 264/22 |
| 4,535,020 | 8/1985 | Thomas et al. | 428/131 |
| 4,609,518 | 9/1986 | Curro et al. | 264/504 |
| 4,629,643 | 12/1986 | Curro et al. | 428/131 |
| 4,695,422 | 9/1987 | Curro et al. | 264/504 |
| 4,777,081 | 10/1988 | Crass et al. | 428/215 |
| 4,839,216 | 6/1989 | Curro et al. | 428/134 |
| 4,876,146 | 10/1989 | Isaka et al. | 428/347 |
| 4,956,232 | 9/1990 | Balloni et al. | 428/349 |
| 5,006,394 | 4/1991 | Baird | 428/138 |
| 5,261,899 | 11/1993 | Visscher et al. | 604/367 |

FOREIGN PATENT DOCUMENTS

| | | |
|---|---|---|
| 0152883 | 8/1985 | European Pat. Off. . |
| 0175259 | 3/1986 | European Pat. Off. . |
| 0257280 | 3/1988 | European Pat. Off. . |
| 0307116 | 3/1989 | European Pat. Off. . |
| 1231569 | 5/1971 | United Kingdom . |

OTHER PUBLICATIONS

Research Disclosure, Durable Hydrophilic Finishes for Olefinic Nonwovens, Films Including Apertured) and Laminates in Disposable Articles, Sep. 1993, p. 593.

*Primary Examiner*—Mathieu D. Vargot
*Attorney, Agent, or Firm*—Kevin C. Johnson; William Scott Andes; E. Kelly Linman

[57] ABSTRACT

A coextruded, multilayer polymeric film having a core layer including a surfactant and at least one outer layer is placed on a forming structure. The forming structure moves in a direction parallel to the direction of travel of the multilayer film and carries the multilayer film in that direction. A fluid pressure differential is applied across the thickness of the multilayer film along the direction of movement of the forming structure. The fluid pressure differential is sufficiently great to cause the multilayer film to conform with the forming structure forming a formed polymeric web. The formed polymeric web is exposed to a temperature which is sufficiently great enough to allow the surfactant in the core layer to migrate to the outer layer to form a surfactant treated formed polymeric web.

18 Claims, 3 Drawing Sheets

PROCESS FOR PRODUCING A SURFACTANT TREATED, FORMED, POLYMERIC WEB

This is a continuation of application Ser. No. 08/204,112, filed on Mar. 1, 1994 now abandoned.

The present invention relates to a process for producing a formed polymeric web, and more particularly, to a process for producing a surfactant treated, formed, polymeric web.

The surfactant treated, formed, polymeric web is particularly well suited for use as a topsheet in absorbent articles such as sanitary napkins, pantiliners, disposable diapers, incontinent articles, and the like.

BACKGROUND OF THE INVENTION

Macroscopically expanded, three-dimensional, apertured polymeric webs are generally known in the art. As used herein, the term "macroscopically expanded", when used to describe three-dimensional plastic webs, ribbons and films, refers to webs, ribbons and films which have been caused to conform to the surface of a three-dimensional forming structure so that both surfaces thereof exhibit the three-dimensional pattern of the forming structure, the pattern being readily visible to the naked eye when the perpendicular distance between the viewer's eye and the plane of the web is about 12 inches. By way of contrast, the term "planar", when used herein to describe plastic webs, ribbons and films, refers to the overall condition of the web, ribbon or film when viewed by the naked eye on a macroscopic scale. In this context "planar" webs, ribbons and films may include webs, ribbons and films having fine-scale surface aberrations on one or both sides, said surface aberrations not being readily visible to the naked eye when the perpendicular distance between the viewer's eye and the plane of the web is about 12 inches or greater.

Examples of macroscopically expanded, three-dimensional, apertured plastic webs which are particularly well suited for use as a topsheet in absorbent articles are disclosed in commonly assigned U.S. Pat. No. 3,929,135 issued to Thompson on Dec. 30, 1975; and in commonly assigned U.S. Pat. No. 4,342,314 issued to Radel et al. on Aug. 3, 1982. Said patents being hereby incorporated herein by reference.

A prior art process for producing macroscopically expanded, three-dimensional, apertured plastic webs is disclosed in commonly assigned U.S. Pat. No. 4,609,518 issued to Curro et al. on Sep. 2, 1986, which is hereby incorporated herein by reference. The patent to Curro et al. discloses a continuous, multi-phase process for debossing and perforating a substantially continuous web of substantially planar polymeric film to coincide with the image of one or more forming structures each having a patterned forming surface with a multiplicity of apertures. A fluid pressure differential is applied across the thickness of the web of film to cause the web of film to conform with the forming structure. While this process has been found to be particularly well suited for forming polymeric webs into various structures, application of the fluid pressure differential across the thickness of the web of film washes away surfactants within the film which are exposed to the fluid during the forming operation. Accordingly, when the formed webs are placed in their end use, i.e., as a topsheet in an absorbent article, such as a disposable diaper or sanitary napkin, they do not have the desired surface properties as the surfactant has been removed during the forming operation.

It is an object of the present invention to provide a process for producing surfactant treated formed polymeric webs where the material is of such a structure that the surfactant is not removed during the forming operation.

It is another object of the present invention to provide a process for producing a surfactant treated formed polymeric web wherein a fluid pressure differential is applied across the thickness of the film to cause the film to conform with a forming structure.

SUMMARY OF THE INVENTION

The present invention pertains, in a particularly preferred embodiment, to a process for making a surfactant treated formed polymeric web. A multilayer polymeric film having a core layer and at least one outer layer is coextruded. The core layer includes a surfactant while the outer layer is preferably devoid of surfactant.

Preferably, the coextruded multilayered film is stored in a controlled temperature environment to prevent the surfactant in the core layer from migrating to the outer layer. The multilayered film is then supported on a forming structure which exhibits a multiplicity of apertures which place the opposed surfaces of the forming structure in fluid communication with one another. The forming structure moves in a direction parallel to the direction of travel of the multilayer film and carries the multilayer film in that direction. A fluid pressure differential is applied across the thickness of the multilayer film along the direction of movement of the forming structure before the surfactant in the core layer migrates to the outer layer. The fluid pressure differential is sufficiently great enough to cause the multilayer film to conform with the forming structure forming a formed polymeric web. In a preferred embodiment, the fluid pressure differential is sufficiently great enough to rupture the multilayer film in those areas coinciding with the apertures in the forming structure. The surfactant in the core layer of the formed polymeric web is allowed to migrate to the outer layer by exposing the formed polymeric web to a temperature sufficiently great enough to allow the core layer to migrate to the outer layer of the formed polymeric web forming a surfactant treated formed polymeric web.

BRIEF DESCRIPTION OF THE DRAWINGS

While the specification concludes with claims particularly pointing out and distinctly claiming the present invention, it is believed that the present invention will be better understood from the following description in conjunction with the accompanying drawings in which:

DETAILED DESCRIPTION OF THE INVENTION

While the present invention will be described in the context of providing a surfactant treated, macroscopically expanded, three-dimensional, apertured plastic web particularly well suited for use as a wearer contacting surface on absorbent articles such as disposable diapers, sanitary napkins, incontinent articles and the like, the present invention is in no way limited to such applications. To the contrary, the present invention may be practiced to great advantage whenever it is desired to produce plastic films or webs exhibiting properties and characteristics not previously obtainable using prior art single-phase and multi-phase web forming processes. The detailed description of the structures disclosed herein and their suggested use as a topsheet and/or backsheet in a disposable absorbent article will allow one skilled in the art to readily adapt the present invention to produce webs well suited to other applications.

Figure 1:
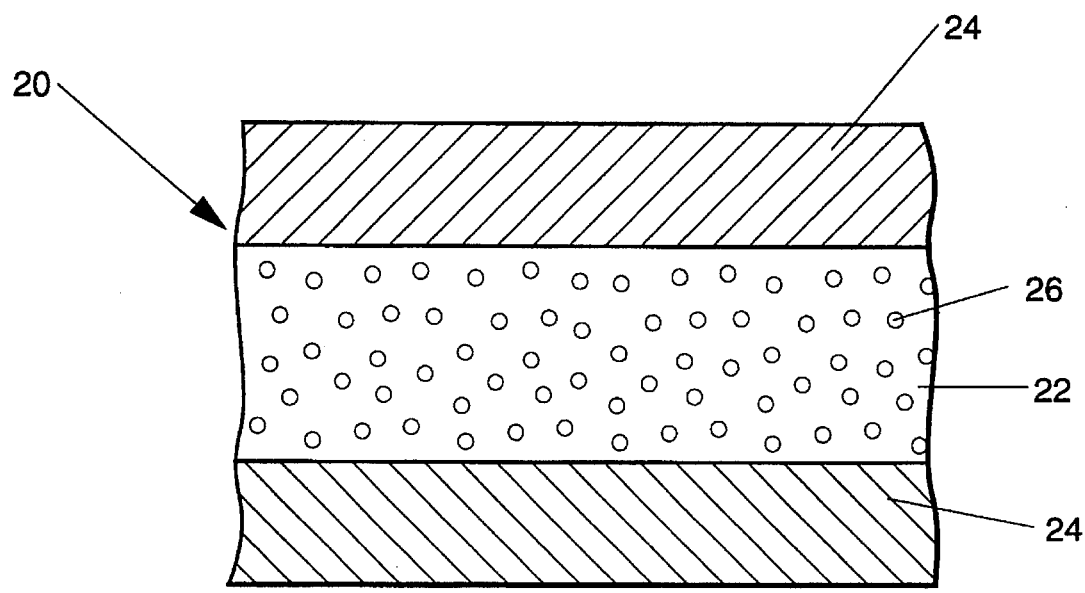
FIG. 1 is a cross-sectional view of a preferred embodiment of a coextruded multilayer film of the present invention, having one core layer and two outer layers.

Referring now to FIG. 1 there is shown a preferred embodiment of a coextruded multilayer polymeric film 20 of the present invention. The multilayer film 20 includes a central core layer 22 and two outer layers 24. The central core layer 22 has opposed first and second sides, each side being substantially continuously joined to one side of one of the outer layers 24.

Preferred polymeric materials for the core layer 22 and the outer layers 24 include polyolefins, particularly polyethylenes, polypropylene and copolymers having at least one olefinic constituent. Other materials such as polyesters, nylons, copolymers thereof and combinations of any of the foregoing may also be suitable for the core layer 22 and the outer layers 24.

The core layer 22 preferably includes a surfactant 26 while the outer layers 24 are initially devoid of suffactants. Surfactant molecules are compounds composed of chemical groups having opposing solubility tendencies within the same molecule. Typically one group is an non-polar/oil-soluble/water insoluble/hydrophobic hydrocarbon chain and the opposing group is a polar/water-soluble/hydrophilic group. Suffactants are classified according to the electrical charge of the polar surface active moiety. In anionic suffactants the polar group carries a negative charge. In cationic surfactants the group carries a positive charge. In amphoteric suffactants both positive and negative charges are present in the same molecule. In non-ionic suffactants, there is no electrical charge on the molecule. The polar hydrophilic group in non-ionic suffactants can be a chain of water soluble ethylene oxide units or a group bearing multiple hydroxyl functionalities, for example groups derived from glycerol or sorbitol. The chemistry of suffactants is very broad and is described more fully in the Kirk-Othmer Encyclopedia of Chemical Technology, 3rd Edition, Volume 22, pp. 332–432, herein incorporated by reference.

In the process of the present invention, suffactants from each class disclosed above can be used in core layer 22. However, where the resulting macroscopically expanded, three dimensional, apertured plastic web is to be used in absorbent articles such as sanitary napkins, pantiliners, disposable diapers, incontinent articles, and the like, where contact with human skin tissue is expected, the skin irritation potential of the surfactant must be considered. In general, cationic suffactants tend to be more irritating than anionic, which tend to be more irritating than either amphoteric or non-ionic types. Preferred surfactants include those from non-ionic families such as: alcohol ethoxylates, alkylphenol ethoxylates, carboxylic acid esters, glycerol esters, polyoxyethylene esters of fatty acids, polyoxyethylene esters of aliphatic carboxylic acids related to abietic acid, anhydrosorbitol esters, ethoxylated anhydrosorbitol esters, ethoxylated natural fats, oils, and waxes, glycol esters of fatty acids, carboxylic amides, diethanolamine condensates, monoalkanolamine condensates, polyoxyethylene fatty acid amides, polyalkyleneoxide block copolymers.

The molecular weights of surfactants selected for the present invention may range from about 200 grams per mole to about 10,000 grams per mole. Preferred surfactants have a molecular weight from about 300 to about 1000 grams per mole.

The surfactant level initially blended into core layer 22 can be as much as 10 percent by weight of the total multilayer structure (core layer 22 plus outer layers 24). Surfactants in the preferred molecular weight range (300–1000 grams/mole) can be added at lower levels, generally at or below about 5 weight percent of the total multilayer structure.

The multilayer film 20 of the present invention may be processed using conventional procedures for producing multilayer films on conventional coextruded film-making equipment. Where layers comprising blends are required, pellets of the above described components can be first dry blended and then melt mixed in the extruder feeding that layer. Alternatively, if insufficient mixing occurs in the extruder, the pellets can be first dry blended and then melt mixed in a precompounding extruder followed by repelletization prior to film extrusion.

In general, polymers can be melt processed into films using either cast or blown film extrusion methods both of which are described in "Plastics Extrusion Technology" —2nd Ed., by Allan A. Griff (Van Nostrand Reinhold— 1976), herein incorporated by reference. Cast film is extruded through a linear slot die. Generally, the flat web is cooled on a large moving polished metal roll. It quickly cools, and peels off the first roll, passes over one or more auxiliary rolls, then through a set of rubber-coated pull or "haul-off" rolls, and finally to a winder.

In blown film extrusion the melt is extruded upward through a thin annular die opening. This process is also referred to as tubular film extrusion. Air is introduced through the center of the die to inflate the tube and causes it to expand. A moving bubble is thus formed which is held at constant size by control of internal air pressure. The tube of film is cooled by air blown through one or more chill rings surrounding the tube. The tube is next collapsed by drawing it into a flattening frame through a pair of pull rolls and into a winder.

A coextrusion process requires more than one extruder and either a coextrusion feedblock or multi-manifold die system or combination of the two to achieve the multilayer film structure.

U.S. Pat. Nos. 4,152,387, and 4,197,069, both herein incorporated by reference, disclose the feedblock principle of coextrusion. Multiple extruders are connected to the feedblock which employs moveable flow dividers to proportionally change the geometry of each individual flow channel in direct relation to the volume of polymer passing through said flow channels. The flow channels are designed such that at their point of confluence, the materials flow together at the same flow rate and pressure eliminating interfacial stress and flow instabilities. Once the materials are joined in the feedblock, they flow into a single manifold die as a composite structure. It is important in such processes that the melt viscosities and melt temperatures of the material do not differ too greatly. Otherwise flow instabilities can result in the die leading to poor control of layer thickness distribution in the multilayer film.

An alternative to feedblock coextrusion is a multi-manifold or vane die as disclosed in aforementioned U.S. Pat. Nos. 4,152,387, 4,197,069, and in U.S. Pat. No. 4,533,308, herein incorporated by reference. Whereas in the feedblock system melt streams are brought together outside and prior to entering the die body, in a multimanifold or vane die each melt stream has its own manifold in the die where the polymers spread independently in their respective manifolds. The melt streams are married near the die exit with each melt stream at full die width. Moveable vanes provide adjustability of the exit of each flow channel in direct proportion to the volume of material flowing through it, allowing the melts to flow together at the same linear flow rate, pressure, and desired width.

Since the melt flow properties and melt temperatures of polymers vary widely, use of a vane die has several advantages. The die lends itself toward thermal isolation characteristics wherein polymers of greatly differing melt temperatures, for example up to 175° F. (80° C.), can be processed together.

Each manifold in a vane die can be designed and tailored to a specific polymer. Thus the flow of each polymer is influenced only by the design of its manifold, and not forces imposed by other polymers. This allows materials with greatly differing melt viscosities to be coextruded into multilayer films. In addition, the vane die also provides the ability to tailor the width of individual manifolds, such that an internal layer can be completely surrounded by the outer layer leaving no exposed edges. The aforementioned patents also disclose the combined use of feedblock systems and vane dies to achieve more complex multilayer structures.

The multilayer films of the present invention may comprise two or more layers. In general, balanced or symmetrical three-layer and five-layer films are preferred. Balanced three-layer multilayer films, like the multilayer film 20, comprise a central core layer 22 and two identical outer layers 24, wherein the central core layer 22 is positioned between the two outer layers 24. Balanced five-layer multilayer films comprise a central core layer, two identical tie layers, and two identical outer layers, wherein the central core layer is positioned between the central core layer and each outer layer. Balanced films, though not essential to the films of the present invention, are less prone to curling or warping than unbalanced multilayer films.

In three-layer films, the central core layer may comprise from about 10 to 90 percent of the films' total thickness and each outer layer may comprise from abut 5 to 45 percent of the films' total thickness. Tie layers, when employed, may each comprise from about 5 percent to about 10 percent of the films' total thickness.

Figure 2:
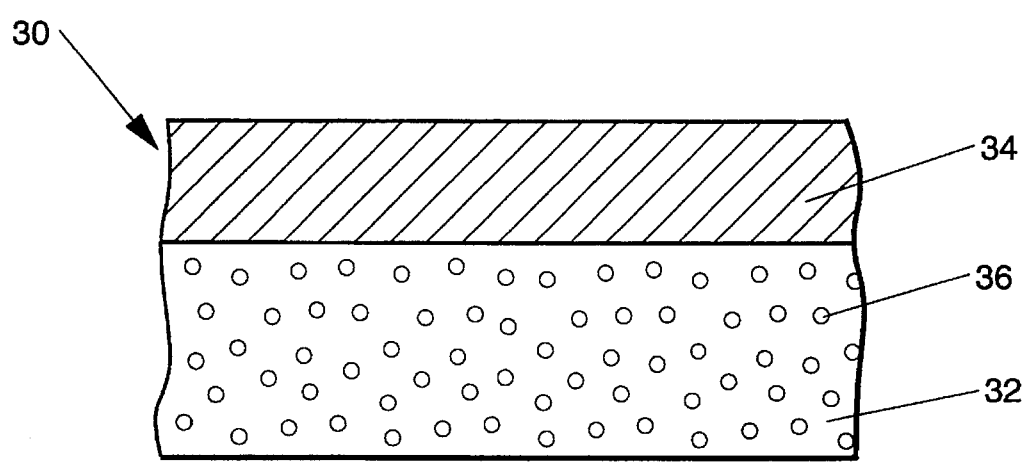
FIG. 2 is a cross-sectional view of another preferred embodiment of a coextruded multilayer film of the present invention, having one core layer and one outer layer.

An example of an unbalanced two-layer multilayer film is the multilayer film 30 illustrated in FIG. 2. The multilayer film 30 comprises a core layer 32 and an outer layer 34. The core layer has opposed first and second sides, one side being substantially continuously joined to one side of the outer layer 34. The core layer 32 preferably includes a surfactant 36 while the outer layer 34 is initially devoid of surfactant.

Figure 3:
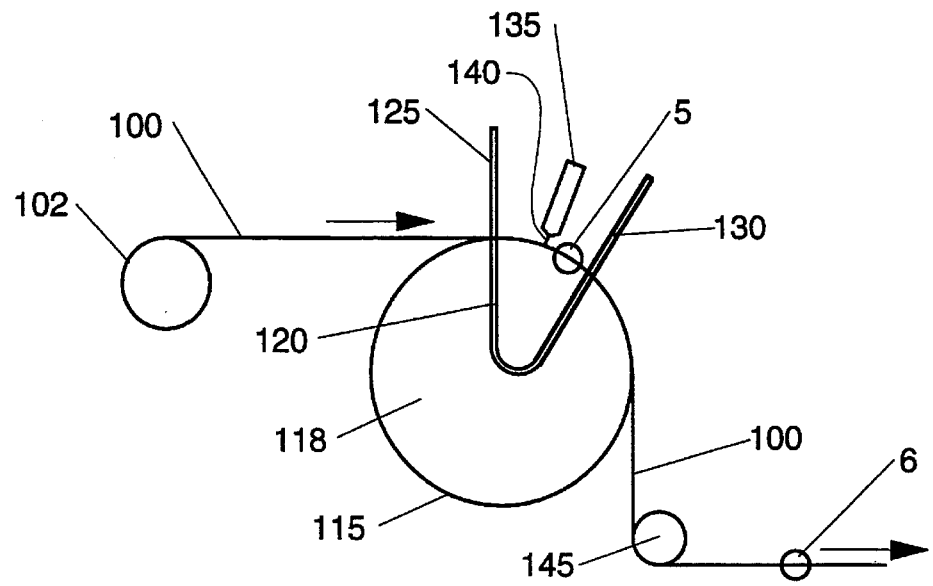
FIG. 3 is a simplified schematic illustration of a film forming process of the present invention.

After the multilayer polymeric film has been coextruded it is preferably fed to a winding station and then stored for a period of time before being formed into a formed polymeric web. A particularly preferred forming process is schematically illustrated in FIG. 3. In the embodiment shown in FIG. 3, a web of substantially planar, coextruded, multilayer film 100 is fed from a supply roll 102 onto the surface of a forming drum 118 about which a forming structure 115 continuously rotates at substantially the same speed as the incoming web. The forming drum 118 preferably includes an internally located vacuum chamber 120 which is preferably stationary relative the moving forming structure 115. A pair of stationary baffles 125, 130 approximately coinciding with the beginning and the end of the vacuum chamber 120 are located adjacent the exterior surface of the forming structure. Intermediate the stationary baffles 125, 130 there is preferably provided means for applying a fluid pressure differential to the substantially planar, multilayer polymeric web of film 100 as it passes across the suction chamber. In the illustrated embodiment, the fluid pressure differential applicator means comprises a high pressure liquid nozzle 135 which discharges a jet of liquid 140, such as water, substantially uniformly across the entire width of the web 100. Details as to the construction, positioning and operating pressure of liquid nozzle 135 are fully set forth in commonly assigned U.S. Pat. No. 4,695, 422 issued to Curro et al. on Sept. 22, 1987, said patent being hereby incorporated by reference.

The jet of liquid 140 is preferably applied across the thickness of the multilayer film before the surfactant in the core layer migrates to the outer layer. If the surfactant migrates to the outer layer or layers of the multilayer film from the core layer, prior to the application of the jet of liquid 140, the surfactant will then be exposed to the jet of liquid and a portion of the surfactant will likely be washed away during the formation step. In order to maintain the surfactant within the core layer of the multilayer film prior to the application of the fluid pressure differential across the thickness of the multilayer film, the coextruded multilayer film is stored below a temperature which is sufficiently great enough to allow the surfactant in the core layer to migrate to the outer layer of the multilayer film. After having been stored in a controlled temperature environment, the web of multilayer film is then introduced to the forming step wherein the formation process may take place without exposing the surfactant, which is in the core layer, to the jet of liquid 140 from nozzle 135. For a given polymer/ surfactant combination, the rate at which the surfactant originally in the core layer will migrate through the outer layer or layers is primarily a function of the thickness of the outer layers, the concentration of surfactant initially in the core layer, and temperature.

Increasing the thickness of the outer layer or layers increases the amount of time needed for the surfactant to migrate to the outermost surface or surfaces of the multilayer film. Conversely, decreasing the thickness of the outer layer or layers decreases the time needed for surfactant migration to the outermost surfaces.

The rate of surfactant migration from the core layer through the outer layer or layers will generally increase with increasing surfactant concentration. However, a significantly high concentration of surfactant in the core layer can cause film processing problems and may cause the surfactant to migrate too fast even at lower temperatures. Conversely, a low concentration of surfactant in the core layer may not allow the desired surface properties of the multilayer formed film to be achieved.

The rate of surfactant migration generally increases with increasing temperature and decreases with decreasing temperature. The lower the temperature, the longer the surfactant will be maintained in the core layer. Conversely, the higher the temperature, the quicker the surfactant will migrate into and through the outer layer or layers. To prevent the surfactant from migrating prematurely, the multilayer film can be stored under controlled conditions, at about room temperature (70° F.) or below, preferably not lower than normal refrigerator or freezer temperatures (32°–40° F.). This can prevent substantial surfactant migration to the films outer surface for several hours to several weeks. Accordingly, the time required to produce a surfactant treated formed polymeric web, one where the surfactant has migrated to the outer layer or layers from the core layer, may be reduced significantly by storing the formed polymeric web in a controlled temperature environment at room temperature or above, preferably less than about 140° F.

Figure 4:
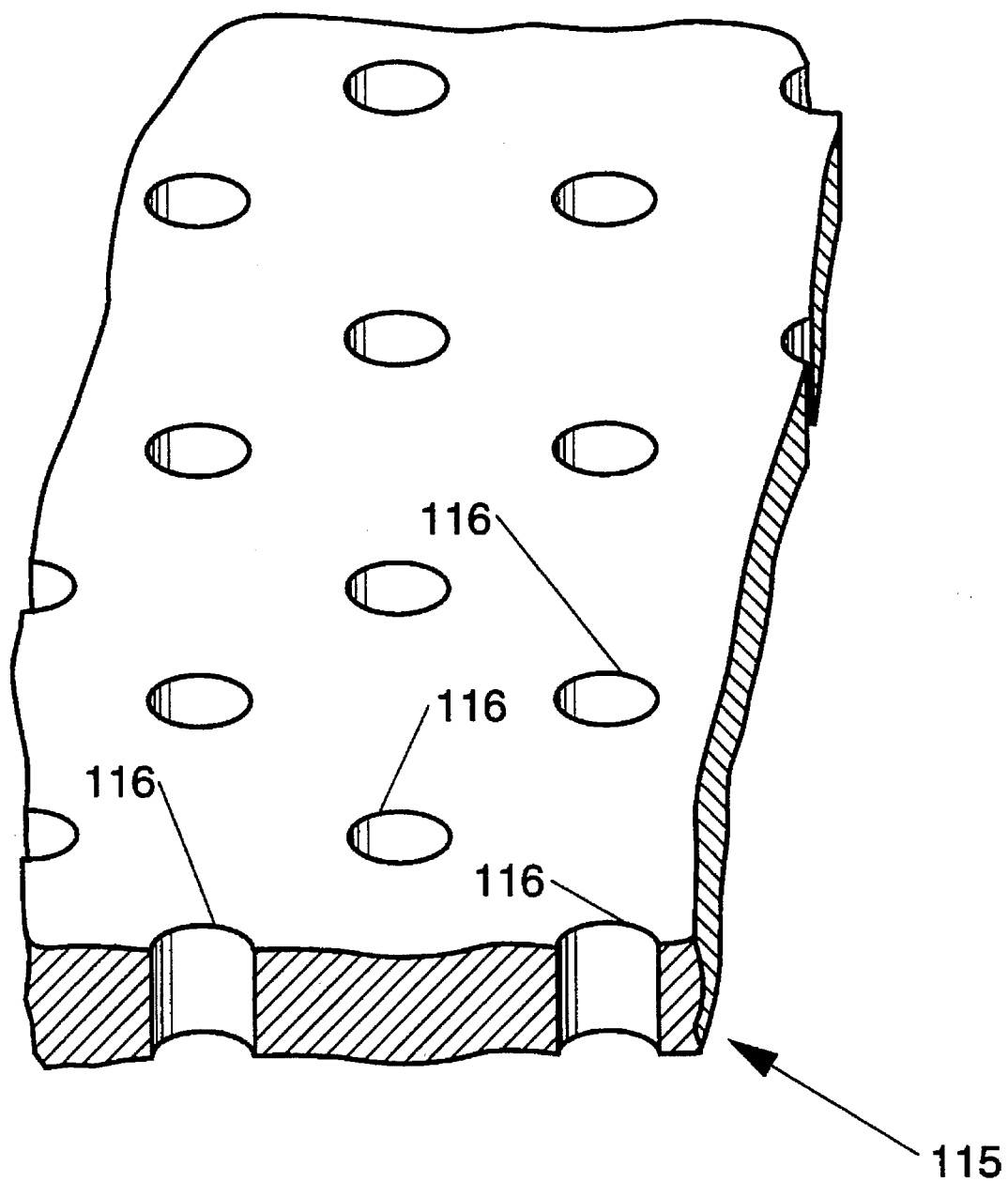
FIG. 4 is a greatly enlarged fragmentary view of a forming structure utilized to support the multilayer film when the film is subjected to a fluid pressure differential generally in accordance with the process illustrated in FIG. 3.

Forming structure 115, a greatly enlarged fragmentary perspective segment of which is illustrated in FIG. 4, includes a multiplicity of relatively small apertures 116 across all or any desired portion of its surface. For disposable diaper topsheet applications these apertures typically range in the size of between about 1 mil. and about 10 mils. in diameter. Their spacing may be in a regular pattern or it may vary randomly, as desired, in the resultant web. Methods of constructing suitable three-dimensional tubular forming members of this general type are disclosed in commonly assigned U.S. Pat. No. 4,508,256 issued to Radel et al. on Apr. 2, 1985 and commonly assigned U.S. Pat. No. 4,509,908 issued to Mullane, Jr. on Apr. 9, 1985, said patents being hereby incorporated by reference.

The apertures 116 and the forming structure 115 may be of any desired shape or cross-section when the forming structure is fabricated utilizing the laminar construction techniques generally disclosed in the aforementioned commonly assigned patents.

Alternatively, the tubular shaped forming structure 115 may be comprised of non-laminar construction and the desired pattern of apertures 116 created by means of laser drilling or the like. It is also possible to use belts or the like comprised of pliable material and operating continuously about a pair of rolls. In the latter circumstance it is generally desirable to provide suitable support beneath the pliable belt when it is subjected to the fluid pressure differential to avoid distortion.

Figure 5:
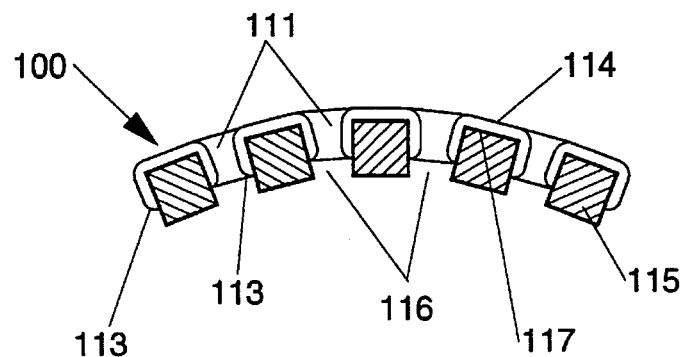
FIG. 5 is a greatly enlarged inset showing, in simplified terms, the condition of the multilayer film after it has been subjected to a fluid pressure differential on a forming structure.

Whatever the origin of the incoming web of polymeric material 100, after it passes beneath a jet of liquid 140, its condition will be generally as shown in the greatly enlarged inset of FIG. 5. At this point, fine-scale apertures 111 corresponding to the relatively small apertures 116 in forming structure 115 have been created in the film 100. The small volcano-like cusps 113 formed about the edge of each aperture 111 reflect a degree of thinning of the film just prior to rupture.

Figure 6:
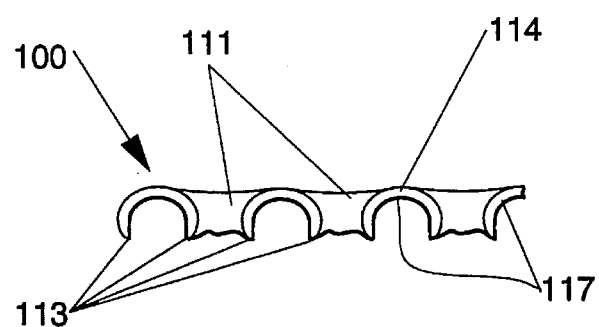
FIG. 6 is a greatly enlarged inset of a formed polymeric web after it has been removed from the forming structure.

Following application of the fluid pressure differential to the film, the finely apertured formed polymeric web 100 is removed from the surface of the forming structure 115 about an idler roll 145 in the condition illustrated in greatly enlarged form in the inset of FIG. 6. Because of the presence of the cusps 13 surrounding each of the tiny apertures 111, the surface 117 which contacted forming structure 115 exhibits a much softer tactile impression than the surface 114 which was contacted by the liquid jet 140. Accordingly, surface 117 of the web is generally preferred as a wearer contacting surface over surface 114.

At the completion of this phase, the finely apertured formed polymeric web 100 may be utilized without further processing in an end product wherein fluid permeability and soft tactile impression are particularly desirable, but a macroscopically expanded, three-dimensional cross-section is not essential.

Alternatively, the formed polymeric web may be fed to a second phase for macroscopic expansion, or to a rewind station for temporary storage. In the former circumstance, the finely apertured formed polymeric web is fed onto a second forming structure to undergo macroscopic, three-dimensional expansion. Examples of suitable forming structures are disclosed in commonly assigned U.S. Pat. No. 4,342,314 issued to Radel et al. on Aug. 3, 1982 and commonly assigned U.S. Pat. No. 4,463,045 issued to Ahr et al. on Jul. 31, 1984. Said patents being incorporated herein by reference. In the latter circumstance, application of the additional phase of the process may be deferred to a later date, perhaps at a different location.

After the formation of the formed polymeric web is complete, the surfactant within the core layer of the formed polymeric web is allowed to migrate to the outer layer(s), thereby forming a surfactant treated formed polymeric web. The surfactant within the core layer of the formed polymeric web is allowed to migrate to the outer layer(s) by exposing the formed polymeric web to a temperature sufficiently great enough to allow the surfactant in the core layer to migrate to the outer layer or layers. By keeping the surfactant within the core layer during the forming step the jet of liquid 140 does not wash the surfactant away as would be the case if the surfactant were placed in the outer layer 24 during the coextrusion step, thereby exposing the surfactant to the jet of liquid 140.

It is believed that the description contained herein will enable one skilled in the art to practice the present invention in many and varied forms. Nonetheless, the following exemplary embodiment is set forth for purposes of illustration:

Example I:

A low density polyethylene (Quantum Chemical Corp., NA-951-00), surfactant concentrate (5% Atmer 645 in polyethylene) and pigment concentrate (Quantum Chemical Corp., CM80582 $TiO_2$ concentrate), all in pellet form, are mixed in the weight ratio 77/15/8 respectively in a paddle mixer (Kelly Duplex). This mixture may then be extruded from an NRM (John Brown Plastics Machinery, Inc.) 2 ½", 30/1 L/D, single screw extruder, outfitted with a general purpose polyolefin screw. The extruder barrel is heating using four heating zones set at temperatures of 211° F., 340° F., 420° F., and 460° F. and increasing monotonically from barrel beginning to barrel end. Concurrently low density polyethylene (Quantum Chemical Corp., NA-951-00) that is devoid of pigment and surfactant is extruded from two 30 mm extruders (Zahnradwerk Kollman) equipped with general purpose polyolefin screws. Both extruders are heated from barrel beginning to barrel end in two heating zones set at temperatures of 340° F., and 460° F. respectively, The outputs of all three extruders are channeled through adapters, maintained at 460° F., to a 24" wide, flex lip, variable vane, three layer, coextrusion film die (Cloeren Co.). The die has nine heating zones, three for each layer. The controller set-points are 460° F. at all edge heating zones and 400° F. at all center heating zones. The die lips are opened about 0.040" and the vanes set to mid position. Draw down, cooling, slitting and windup of the film are accomplished with a Johnson (John Brown Plastics Machinery, Inc.) take-off system. The polished rolls are maintained at about room temperature and the haul-off rate is 82 feet per minute. Extruder output rates are adjusted to provide a film about 0.0012" thick, comprised of about 60% surfactant containing polyethylene as the middle layer and about 20% virgin polyethylene for each outer layer.

The roll is placed in refrigeration at about 40° F., for a period of time, preferably more than 12 hours. The roll is then removed from refrigeration and is subjected to a forming operation similar to that illustrated in FIG. 3. Preferably, the forming operation takes place in a location at ambient temperature.

While particular embodiments of the present invention have been illustrated and described, it would be obvious to those skilled in the art that various other changes and modifications can be made without departing from the spirit and scope of the present invention. It is therefore intended to cover in the appended claims all such changes and modifications that are within the scope of this invention.

What is claimed:

1. A process for making a surfactant treated formed polymeric web, said process comprising the steps of:
   (a) coextruding a multilayer polymeric film, said multilayer film including a core layer and at least one outer layer, said core layer including a surfactant, said outer layer being initially devoid of surfactant;
   (b) supporting said multilayer film on a forming structure, said forming structure moving in a direction parallel to the direction of travel of said multilayer film and carrying said multilayer film in said direction;
   (c) applying a fluid pressure differential across the thickness of said multilayer film along said direction of movement of said forming structure before said surfactant in said core layer migrates to said outer layer, said fluid pressure differential being sufficiently great to cause said multilayer film to conform with said forming structure forming a formed polymeric web; and
   (d) exposing said formed polymeric web to a temperature which is sufficiently great enough to allow said surfactant in said core layer to migrate to said outer layer of said formed polymeric web forming a surfactant treated formed polymeric web.

2. The process of claim 1, further comprising the step of storing said multilayer film below a temperature which is sufficiently great enough to allow said surfactant in said core layer to migrate to said outer layer of said multilayer film prior to supporting said multilayer film on a forming structure.

3. The process of claim 1, wherein said multilayer film includes two outer layers.

4. The process of claim 3, wherein both of said outer layers of said multilayer film are initially devoid of surfactant.

5. The process of claim 1, wherein said forming structure exhibits a multiplicity of apertures which place the exposed surfaces of said forming structure in fluid communication with one another.

6. The process of claim 5, wherein said fluid pressure differential is sufficiently great to cause said multilayer film to rupture in those areas coinciding with the apertures in said forming structure.

7. A process for making a surfactant treated formed polymeric web, said process comprising the steps of:
   (a) coextruding a multilayer polymeric film, said multilayer film including a core layer and at least one outer layer, said core layer including a surfactant, said outer layer being initially devoid of surfactant;
   (b) supporting said multilayer film on a forming structure exhibiting multiplicity of apertures which place the opposed surfaces of said forming structure in fluid communication with one another, said forming structure moving in a direction parallel to the direction of travel of said multilayer film and carrying said multilayer film in said direction;
   (c) applying a fluid pressure differential across the thickness of said multilayer film along said direction of movement of said forming structure before said surfactant in said core layer migrates to said outer layer, said fluid pressure differential being sufficiently great to cause said multilayer film to rupture in those areas coinciding with said apertures in said forming structure forming a formed polymeric web; and
   (d) exposing said formed polymeric web to a temperature which is sufficiently great enough to allow said surfactant in said core layer to migrate to said outer layer of said formed polymeric web forming a surfactant treated formed polymeric web.

8. The process of claim 7, further comprising the step of storing said multilayer film below a temperature which is sufficiently great enough to allow said surfactant in said core layer to migrate to said outer layer of said multilayer film prior to supporting said multilayer film on a forming structure.

9. The process of claim 7, wherein said multilayer film includes two outer layers.

10. The process of claim 9, wherein both of said outer layers of said multilayer film are initially devoid of surfactant.

11. A process for making a surfactant treated formed polymeric web, said process comprising the steps of:
    (a) coextruding a multilayer polymeric film, said multilayer film including a core layer and at least one outer layer, said core layer including a surfactant, said outer layer being initially devoid of surfactant;
    (b) storing said multilayer film below a temperature which is sufficiently great enough to allow said surfactant in said core layer to migrate to said outer layer of said multilayer film;
    (c) supporting said multilayer film on a forming structure, said forming structure moving in a direction parallel to the direction of travel of said multilayer film and carrying said multilayer film in said direction;
    (d) applying a fluid pressure differential across the thickness of said multilayer film along said direction of movement of said forming structure before said surfactant in said core layer migrates to said outer layer, said fluid pressure differential being sufficiently great to cause said multilayer film to conform with said forming structure forming a formed polymeric web; and
    (e) exposing said formed polymeric web to a temperature which is sufficiently great enough to allow said surfactant in said core layer to migrate to said outer layer of said formed polymeric web forming a surfactant treated formed polymeric web.

12. The process of claim 11, wherein said multilayer film includes two outer layers.

13. The process of claim 12, wherein both of said outer layers of said multilayer film are initially devoid of surfactant.

14. The process of claim 11, wherein said forming structure exhibits a multiplicity of apertures which place the exposed surfaces of said forming structure in fluid communication with one another.

15. The process of claim 14, wherein said fluid pressure differential is sufficiently great to cause said multilayer film to rupture in those areas coinciding with the apertures in said forming structure.

16. The process of claim 1, wherein said fluid pressure differential is applied via a high pressure liquid nozzle which discharges a jet of liquid.

17. The process of claim 7, wherein said fluid pressure differential is applied via a high pressure liquid nozzle which discharges a jet of liquid.

18. The process of claim 11, wherein said fluid pressure differential is applied via a high pressure liquid nozzle which discharges a jet of liquid.

* * * * *